United States Patent [19]

Yamada et al.

[11] Patent Number: 4,661,456

[45] Date of Patent: * Apr. 28, 1987

[54] METHOD FOR CULTIVATION OF PSEUDOMONAS BACTERIA

[75] Inventors: Hideaki Yamada, 19-1, Matsugasaki-Kinomoto-Cho, Sakyo-Ku, Kyoto-Shi, Kyoto-Fu; Koitchiro Ryuno; Kanehiko Enomoto, both of Yokohama; Ichiro Watanabe, Yokosuka, all of Japan

[73] Assignees: Nitto Kagaku Kogyo Kabushiki Kaisha, Tokyo; Hideaki Yamada, Kyoto, both of Japan

[ * ] Notice: The portion of the term of this patent subsequent to Apr. 28, 2004 has been disclaimed.

[21] Appl. No.: 569,021

[22] Filed: Jan. 9, 1984

[30] Foreign Application Priority Data

Oct. 13, 1983 [JP] Japan .................................. 58-191636

[51] Int. Cl.$^4$ ........................... C12N 1/38; C12N 9/78; C12N 1/20; C12R 1/38
[52] U.S. Cl. .................................... 435/244; 435/227; 435/253; 435/874
[58] Field of Search ................. 435/227, 244, 874, 253

[56] References Cited

U.S. PATENT DOCUMENTS

| | | | |
|---|---|---|---|
| 3,989,592 | 11/1976 | Leavitt ................................. | 435/874 |
| 4,001,081 | 1/1977 | Commeyras et al. ................ | 435/832 |
| 4,390,631 | 6/1983 | Watanabe et al. ................... | 435/129 |
| 4,440,858 | 4/1984 | Yamaguchi et al. ................. | 435/129 |

FOREIGN PATENT DOCUMENTS

58-01784 5/1983 Japan .................................... 435/129

OTHER PUBLICATIONS

Agricultural and Biological Chemistry (1976), vol. 40, No. 8, pp. 1515–1522.
Journal of Fermentation Technology (1974), vol. 52, p. 567.
Journal of Fermentation Technology, vol. 50, (1972), p. 637.
Laboratory Methods in Microbiology (1966), pp. 38–41.
Journal of General and Applied Microbiology (1982), vol. 28, pp. 359–368.
Manual of Clinical Microbiology, 2nd Ed. (1974), American Society for Microbiology Washington, D.C., p. 896.
Asano et al., Agricultural Biological Chemistry (1982), vol. 46, pp. 1165–1174.
Asano et al, Agricultural Biological Chemistry (1982), vol. 46, pp. 1175–1181.

*Primary Examiner*—Sidney Marantz
*Assistant Examiner*—William J. Herald
*Attorney, Agent, or Firm*—Robert E. Burns; Emmanuel J. Lobato; Bruce L. Adams

[57] ABSTRACT

Cells of Pseudomonas bacteria having a high nitrile hydratase activity can be obtained in a high yield by adding to a culture medium at least one α-amino acid, except for cysteine or cystine alone and a combination of these α-amino acids alone, in the preparation of cells of bacteria having nitrile hydratase activity by cultivating under nitrile hydratase-inducing conditions Pseudomonas bacteria capable of producing nitrile hydratase.

8 Claims, No Drawings

METHOD FOR CULTIVATION OF PSEUDOMONAS BACTERIA

BACKGROUND OF THE INVENTION

The present invention relates to a method of producing in a high yield cells of Pseudomonas bacteria having a high nitrile hydratase activity.

In recent years, the technology of immobilized enzymes or microorganisms has developed rapidly, resulting in increasing attempts to utilize microorganisms and enzymes as they are or in an immobilized state as catalysts for various single or complex chemical reactions.

Nitrile hydratase has been found by Hideaki Yamada, one of the present inventors, et al. as an enzyme capable of hydrating nitriles to produce the corresponding amides. (Reference: Agric. Biol. Chem. 46 1165 (1982)) As one example of the utilization of this enzyme, a method for preparation of acrylamide from acrylonitrile in the presence of bacteria having nitrile hydratase has been proposed. (References: Japanese Patent Laid-Open Pub. No. 86093/1983 (Japanese Patent Appln. No. 184688/1981) and Agric. Biol. Chem. 46 1183 (1982))

Under these circumstances, a method that can ensure the production of cells of Pseudomonas bacteria having a high nitrile hydratase activity in a high yield would be remarkably beneficial.

From the foregoing point of view, some of us have proposed a method in Japanese Patent Appln. No. 1997/1983. The method for cultivation of Pseudomonas bacteria disclosed in this Japanese patent application comprises adding cysteine and/or cystin to a culture medium in the preparation of cells of bacteria having nitrile hydratase activity by cultivating under nitrile hydratase-inducing conditions Pseudomonas bacteria capable of producing nitrile hydratase.

SUMMARY OF THE INVENTION

An object of the present invention is to solve the above problem by substantially the same means as is disclosed in the aforesaid Japanese patent application on the basis of the discovery that α-amino acids other than cysteine and cystine have similar advantages.

Thus, a distinguishing feature of the method for cultivation of Pseudomonas bacteria having a high nitrile hydratase activity according to this invention is the addition of at least one α-amino acid, except for cysteine or cystine alone and a combination of these α-amino acids alone, to a culture medium in the preparation of cells of bacteria having nitrile hydratase activity by cultivating under nitrile hydratase-inducing conditions Pseudomonas bacteria capable of producing nitrile hydratase.

We have found that, by adding one or more α-amino acids to the culture medium during the cultivation of Pseudomonas bacteria, the nitrile hydratase activity per unit culture fluid increases remarkably. More specifically, for example, the addition of one or more α-amino acids can increase the nitrile hydratase activity per unit culture fluid to a level nearly twice to five times that obtained when the α-amino acid is not added.

This increase in nitrile hydratase activity per unit culture fluid is presumably traceable to the increase in cell concentration (i.e., yield) and cell activity (i.e., quantity of the nitrile hydratase in the cells).

DETAILED DESCRIPTION OF THE INVENTION

Pseudomonas Bacteria

The bacteria used in the present invention are Pseudomonas bacteria having nitrile hydratase activity and the capability of hydrating nitriles, particularly acrylonitrile, to produce the corresponding amides, particularly acrylamide. Specific examples of such bacteria are Pseudomonas chlororaphis, strain B 23 (FERM BP-187), and Pseudomonas sp., strain PS 1 (FERM BP-188), disclosed in Japanese Patent Laid-Open Pub. No. 86093/1983 mentioned above. The principal microbiological properties of these bacteria are as follows.

TABLE 1

| | | B 23 | PS 1 |
|---|---|---|---|
| (a) | Morphology | | |
| 1 | Shape and size of cell | bacillus 0.8–1.1 × 1.6–2.7 μm | bacillus 0.8–1.1 × 1.3–1.9 μm |
| 2 | Polymorphism | none | none |
| 3 | Motility | motile one to three polar flagella | motile with polar flagella |
| 4 | Formation of spores | none | none |
| 5 | Gram staining | − | − |
| 6 | Acid-fast property | − | − |
| (b) | Growth on various culture media | | |
| 1 | Bouillon-agar plate culture | spherical, convex, glossy, translucent and yellow | smooth, homogeneous, glossy, and mucoidal |
| 2 | Bouillon-agar slant culture | small colony formed | smooth, glossy, translucent, and yellow |
| 3 | Bouillon liquid culture | precipitated | |
| 4 | Bouillon-gelatin stab culture | liquified (+) | − |
| 5 | Litmus-milk | acidic: peptonized, not coagulated | alkaline: peptonized, not coagulated |
| (c) | Physiological properties | | |
| 1 | Reduction of nitrate | + | − |
| 2 | Denitrification | + | − |
| 3 | MR test | − | − |
| 4 | VP test | − | − |
| 5 | Formation of indole | − | − |
| 6 | Formation of hydrogen sulfide | − | − |
| 7 | Hydrolysis of starch | − | − |
| 8 | Utilization of citric acid | Simon's culture: + | Simon's culture: + |
| 9 | Utilization of inorganic nitrogen source | ammonium salt: + | ammonium salt: + |
| 10 | Formation of pigments | King-A culture: − King-B culture: + green (water-soluble) | King-A culture: − King-B culture: + green (water-soluble) |
| 11 | Urease | − | − |
| 12 | Oxidase | + | + |
| 13 | Catalase | + | + |
| 14 | Growth range | pH: 6.0–9.9 temperature: | |

TABLE 1-continued

| | | B 23 | | PS 1 | |
|---|---|---|---|---|---|
| | | 5–36.5° C. | | | |
| 15 | Behavior toward oxygen | aerobic | | aerobic | |
| 16 | O-F Test | oxidized | | oxidized | |
| 17 | Formation of acid & gas from saccharide | Formation of acid | Formation of gas | Formation of acid | Formation of gas |
| | D-glucose | + | − | + | − |
| | D-mannose | + | − | + | − |
| | D-fructose | − | − | − | − |
| | D-galactose | + | − | + | − |
| | maltose | − | − | − | − |
| | sucrose | − | − | − | − |
| | lactose | − | − | − | − |
| | trehalose | | | − | − |
| | D-mannitol | − | − | − | − |
| | glycerol | − | − | − | − |
| | starch | − | − | − | − |
| 18 | Nutritive requirements | none | | none | |
| 19 | Other properties | See remarks | | | |

Remarks:

| | |
|---|---|
| Aminopeptidase | + |
| Formation of levan from saccharose | + |
| Formation of poly-β-hydroxybutyrate | − |
| GC content | 64.6% |

Enzymatic Activity Improving Agent

In the present invention, one or more α-amino acids other than cysteine and cystine are used as enzymatic activity improving agents. These α-amino acids can be used singly or in the form of a mixture of two or more members.

The α-amino acids used in the present invention may be of the L-type, D-type or mixed L- and D-types, and can be used singly or in the form of a mixture of two or more members as has been set forth above. L-typed α-amino acids may be preferred from the point of view of effectiveness while mixtures of D- and L-typed α-amino acids may be preferred from the point of view of easy availability.

Suitable α-amino acids are those which are known as natural protein constituents. Specific examples of such α-amino acids are those whose effectiveness is indicated in Example 1 set forth hereinlater. Especially preferred among these α-amino acids are alanine, valine, methionine, aspartic acid, phenylalanine, proline, and glutamic acid. Of these, methionine, aspartic acid, and glutamic acid are advantageous because of their relatively stable activity. These α-amino acids may be used in the form of a mixture as has been stated hereinbefore, and it is within the purview of the present invention to use cysteine and/or cystine in combination therewith.

Cultivation-Practice of the Present Invention

A preferred embodiment of this invention will be described below.

At least one α-amino acid is added at one time or sequentially to a culture medium containing: carbon sources such as glucose, fructose, sucrose, dextrins, glycerol, ethanol, and succinic acid; nitrogen sources such as ammonia, ammonium sulfate, ammonium chloride, ammonium nitrate, and urea; organic nutriment sources such as yeast extract, meat extract, malt extract, casein hydrolyzate, and peptone; inorganic salts such as phosphates; magnesium, potassium, and iron and like metals in trace amounts; and other substances at a concentration of 0.1 to 10 g/liter, preferably 0.5 to 6.0 g/liter. The term "sequentially" as used herein is intended to mean both "continuously" and "intermittently".

This culture medium is inoculated with Pseudomonas bacteria having nitrile hydratase activity, and cultivation is carried out under aerobic conditions while an enzyme inducing agent is added to induce nitrile hydratase. Examples of the enzyme inducing agent are propionitrile, isobutyronitrile, propionamide, and isobutyramide (Japanese Patent Appln. No. 199750/1982), and acrylamide, methacrylamide, crotonamide, and n-butyramide (Japanese Patent Appln. No. 191637/1983). These enzyme inducing agents are effective when added during the cultivation of bacteria at a concentration ordinarily of lower than 15 g/liter, preferably of 10 g/liter or lower. The pH of the culture medium is of the order of 6 to 9, preferably of the order of 7 to 8, while the cultivation temperature is of the order of 20° to 37° C., preferably of the order of 25° to 30° C., and the cultivation time is about 1 to 3 days.

EXAMPLE 1

1. Cultivation of Bacteria 2 ml of a seed culture fluid obtained from *Pseudomonas chlororaphis*, strain B 23 (FERM BP-187), grown under the following precultivation conditions was cultivated under the following cultivation conditions to determine the acrylamide-producing activity of the bacteria.

(1) Precultivation Conditions
MY Culture Medium (pH 7.6):

| | |
|---|---|
| peptone | 5 g/liter |
| yeast extract | 3 g/liter |
| malt extract | 3 g/liter |
| glucose | 5 g/liter |

Cultivation temperature: 28° C.
Cultivation time: 12 hours
A 500-ml (net capacity: 100 ml) Sakaguchi-flask was used.

(2) Cultivation Conditions
Culture medium (pH 7.6):

| | |
|---|---|
| sucrose | 10 g/liter |
| KH$_2$PO$_4$ | 0.5 g/liter |
| K$_2$HPO$_4$ | 0.5 g/liter |
| MgSO$_4$.7H$_2$O | 20 mg/liter |
| α-amino acid | 2 g/liter |
| isobutyronitrile | 5 ml/liter |

Cultivation temperature: 25° C.
A 500-ml (net capacity: 100 ml) Sakaguchi-flask was used.

2. Measurement of Nitrile Hydratase Activity 1 ml of a culture fluid was admixed with 4 ml of a 1/10M phosphate buffer solution (pH 7.0), and 5 ml of a 1/10M phosphate buffer solution (ph 7.0) containing 5.0% by weight of acrylonitrile was added thereto. The resulting solution was caused to react at 10° C. for 10 minutes, and the bacterium cells therein were separated by filtration. The nitrile hydratase activity of the cells exhibited in the hydration of acrylonitrile to produce acrylamide was determined by measuring the quantity of the acrylamide (AA) thus produced by means of gas chromatography.

The activity was determined for the specific activity (SA) and the total activity (TA) as defined below.

SA: μmole AA/mg-cells/min.
TA: μmole AA/ml-culture medium/min.

The results obtained are summarized in Table 1 in which the activity is shown by the maximum activity value marked.

TABLE 2

| Species of Amino Acid *1 | Cultivation Time (hr) | Cell Concentration (g/liter) *2 | Enzymatic Activity SA | TA |
|---|---|---|---|---|
| DL-Ala | 42 | 3.04 | 23.27 | 70.62 |
| L-Val | 48 | 3.07 | 23.39 | 71.81 |
| L-Met | 36 | 2.04 | 35.53 | 72.48 |
| L-Asp | 36 | 4.48 | 16.88 | 75.28 |
| L-Lys | 48 | 2.28 | 24.55 | 55.97 |
| L-Phe | 42 | 2.90 | 28.19 | 81.85 |
| L-Pro | 36 | 3.18 | 25.72 | 81.79 |
| L-Trp | 42 | 2.16 | 23.26 | 50.24 |
| L-Leu | 39 | 3.16 | 15.84 | 50.05 |
| L-Ile | 32 | 3.28 | 14.10 | 46.25 |
| L-Glu | 26 | 3.36 | 23.05 | 77.45 |
| L-Arg | 26 | 3.54 | 17.90 | 63.37 |
| L-His | 32 | 3.04 | 17.03 | 51.77 |
| L-Tyr | 32 | 2.11 | 23.06 | 48.66 |
| (L-Cys | 32 | 2.44 | 26.08 | 63.64) |
| (L-CysS | 30 | 2.14 | 34.47 | 73.76) |
| — *3 | 42 | 1.80 | 22.22 | 40.00 |

*1 Ala: alanine
Val: valine
Met: methionine
Asp: aspartic acid
Lys: lysine
Phe: phenylalanine
Pro: proline
Trp: tryptophan
Leu: leucine
Ile: isoleucine
Glu: glutamic acid
Arg: arginine
His: histidine
Tyr: tyrosine
Cys: cysteine
CysS: cystine
*2 on a dry cell basis
*3 amino acid not added

EXAMPLE 2

Cultivation was carried out under the same conditions as in Example 1 with combinations of α-amino acids which had been found to be especially effective in Example 1 and cysteine respectively at a concentration of 2 g/liter. The activity is shown by the maximum activity value marked.

TABLE 3

| Species of Amino Acid | Cultivation Time (hr) | Cell Concentration (g/liter) | Enzymatic Activity SA | TA |
|---|---|---|---|---|
| DL-Ala | 31 | 3.58 | 27.35 | 97.91 |
| L-Val | 31 | 3.34 | 27.39 | 91.48 |
| L-Met | 37 | 3.52 | 24.64 | 86.73 |
| L-Asp | 31 | 5.48 | 16.94 | 92.83 |
| L-Phe | 31 | 3.10 | 30.71 | 95.20 |
| L-Pro | 31 | 3.58 | 29.09 | 104.14 |
| L-Glu | 31 | 4.05 | 25.53 | 103.40 |

TABLE 3-continued

| Species of Amino Acid | Cultivation Time (hr) | Cell Concentration (g/liter) | Enzymatic Activity SA | TA |
|---|---|---|---|---|
| — * | 32 | 2.44 | 26.08 | 63.64 |

* L-Cysteine alone

EXAMPLE 3

Cultivation was carried out similarly as in Example 2 by the use of some α-amino acids with the Cys-Glu combination which had been found effective in Example 2, the concentration of the cysteine, glutamic acid and α-amino acid each being 2 g/liter. The activity is shown by the maximum activity value marked.

TABLE 4

| Species of Amino Acid | Cultivation Time (hr) | Cell Concentration (g/liter) | Enzymatic Activity SA | TA |
|---|---|---|---|---|
| L-Phe | 33 | 5.42 | 25.88 | 140.3 |
| L-Pro | 31 | 6.08 | 25.88 | 157.4 |
| L-Asp | 33 | 5.84 | 20.65 | 120.6 |
| DL-Ala | 33 | 6.02 | 22.51 | 135.5 |
| — * | 31 | 4.05 | 25.53 | 103.4 |

* L-cysteine + L-glutamic acid alone.

What is claimed is:

1. A method for increasing the nitrile hydratase activity of Pseudomonas bacteria which comprises providing a a biologically pure culture of Pseudomonas bacteria capable of producing nitrile hydratase, adding to a culture medium an α-amino acid selected from the group consisting of alanine, valine, methionine, aspartic acid, phenylalanine, proline, and glutamic acid, or said α-amino acid together with cysteine and/or cystine and cultivating the Pseudomonas bacteria in the culture medium in the presence of said α-amino acid and an enzyme inducing agent.

2. The method as claimed in claim 1, wherein the concentration of the α-amino acid in the culture medium is in the range of from 0.1 to 10 g/liter.

3. The method as claimed in claim 1, wherein the Pseudomonas bacteria capable of producing nitrile hydratase is *Pseudomonas chlororaphis*, strain B 23 (FERM BP-187), or Pseudomonas sp., strain PS 1 (FERM BP-188).

4. The method as claimed in claim 1, wherein the α-amino acid is selected from the group consisting of alanine, valine, methionine, aspartic acid, phenylalanine, proline and glutamic acid.

5. The method as claimed in claim 1, wherein the α-amino acid is selected from the group consisting of methionine, aspartic acid and glutamic acid.

6. The method as claimed in claim 1 in which the pH of the culture medium is of the order of 6 to 9.

7. The method as claimed in claim 1 in which the enzyme inducing agent is selected from a member of the group consisting of propionitrile, isobutyronitrile, propionamide isobutyramide, acrylamide, methacrylamide, crotonamide and n-butyramide.

8. The method as claimed in claim 1, wherein the α-amino acid comprises a combination of the cysteine, glutamic acid and a member acid selected from alanine, aspartic acid, phenylalanine and proline.

* * * * *